United States Patent [19]

Innes et al.

[11] Patent Number: 4,545,943

[45] Date of Patent: Oct. 8, 1985

[54] FLUIDIZED BED PROCESS FOR PRODUCING ACRYLONITRILE AND CATALYTIC MIXTURE CONTAINING ANTIMONY OXIDE-SILICA COMPOSITE USED THEREIN

[75] Inventors: Robert A. Innes; Harold E. Swift, both of Monroeville, Pa.

[73] Assignee: Gulf Research & Development Co., Pittsburgh, Pa.

[21] Appl. No.: 240,267

[22] Filed: Mar. 4, 1981

[51] Int. Cl.[4] .............................................. C07C 120/14
[52] U.S. Cl. .................................. 260/465.3; 502/240; 502/242; 502/246; 502/249
[58] Field of Search ...................................... 260/465.3

[56] References Cited

U.S. PATENT DOCUMENTS

| | | | |
|---|---|---|---|
| 3,308,151 | 3/1967 | Callahan et al. | 260/465.3 |
| 3,471,545 | 10/1969 | Giordano et al. | 260/465.3 |
| 3,625,867 | 12/1971 | Yoshino et al. | 260/465.3 X |
| 3,627,817 | 12/1971 | Barnett et al. | 260/465.3 |
| 3,686,267 | 8/1972 | Taylor | 260/465.3 |
| 3,818,066 | 6/1974 | Barnett et al. | 260/465.3 |
| 4,040,983 | 8/1977 | Innes et al. | 260/465.3 X |
| 4,045,373 | 8/1977 | Innes et al. | 260/465.3 |
| 4,057,570 | 11/1977 | Innes et al. | 260/465.3 |
| 4,222,899 | 9/1980 | Innes et al. | 260/465.3 X |

*Primary Examiner*—Joseph Paul Brust
*Attorney, Agent, or Firm*—Roylance, Abrams, Berdo & Goodman

[57] ABSTRACT

Acrylonitrile is produced by passing a gaseous mixture comprising propylene, molecular oxygen and ammonia upwardly through a fluidized bed comprising particles of a highly-active acrylonitrile catalyst in physical admixture with particles of a composite consisting essentially of antimony oxide and silica. The use of the antimony oxide-silica composite moderates the effect of the highly-active acrylonitrile catalyst reducing its activity sufficiently to enable the use of longer residence times, but without reducing the acrylonitrile selectivity of the catalyst.

19 Claims, No Drawings

FLUIDIZED BED PROCESS FOR PRODUCING ACRYLONITRILE AND CATALYTIC MIXTURE CONTAINING ANTIMONY OXIDE-SILICA COMPOSITE USED THEREIN

FIELD OF THE INVENTION

This invention relates to a process for producing acrylonitrile in a fluidized bed reactor and to the catalytic bed used therein. More particularly, this invention relates to a fluidized bed process for producing acrylonitrile in which propylene, molecular oxygen and ammonia are passed upwardly through a fluidized bed comprising an admixture of particles of a highly-active acrylonitrile catalyst and particles of an antimony oxide-silica composite, and to the admixture used in the fluidized bed.

DESCRIPTION OF THE PRIOR ART

The use of highly-active catalysts for the conversion of propylene to acrylonitrile in the presence of ammonia and a gas containing molecular oxygen, such as air or pure oxygen, may require residence times of less than about two seconds in order to achieve good acrylonitrile selectivity. Examples of highly-active acrylonitrile catalysts are described in U.S. Pat. Nos. 4,040,983 and 4,045,373, as well as U.S. Pat. No. 4,222,899 to R. A. Innes et al, which catalysts comprise uranium, antimony and a Group IV B element or tin, alone, or in combination with molybdenum and/or vanadium. In a conventional fluidized bed process reactant gases are passed upwardly through a bed of suitable sized catalyst particles at a velocity sufficiently high to buoy the particles and impart to them a violently turbulent fluid-like motion, but not so high as to sweep the bed, or any appreciable portion thereof, out of the reactor. A stable bed is maintained which has a distinct surface resembling a boiling liquid. If highly-active acrylonitrile catalysts are used in conventional commercial fluidized bed reactors, residence times of less than two seconds are difficult to achieve, because the gas velocities required would carry the catalyst particles out of the reactor. In addition, such reactors are not easily equipped to remove the large amounts of heat generated at such high throughputs. Reactors have been proposed which are designed especially to overcome such problems with highly-active catalysts, as for example in U.S. Pat. No. 4,102,914 to H. Beuther, R. A. Innes and H. E. Swift, but acrylonitrile producers may also wish to use such catalysts in their existing conventional facilities.

SUMMARY OF THE INVENTION

It has now been found that a highly-active acrylonitrile catalyst can be effectively used in a fluidized bed reactor without the need for a special reactor configuration, by utilizing a fluidized bed comprising a physical admixture of particles of the highly-active acrylonitrile catalyst and particles of an antimony oxide-silica composite. Surprisingly, the admixture of discrete particles of the antimony oxide-silica composite with discrete particles of highly-active acrylonitrile catalyst provides a catalytic fluidized bed having reduced activity without adversely affecting its acrylonitrile selectivity. Such reduced activity of the resultant catalyst-composite admixture permits the contact time to be lengthened and the concomitant use of lower gas velocities, thereby avoiding the catalyst particle carry over and heat exchange problems normally encountered when one attempts to use a highly-active acrylonitrile catalyst in the absence of the composite of the present invention. Thus, the process of the present invention comprises passing a gaseous mixture comprising propylene, molecular oxygen and ammonia upwardly through a fluidized bed comprising particles of a highly-active acrylonitrile catalyst physically admixed with particles of an antimony oxide-silica composite.

The antimony oxide-silica composite of the present invention can be prepared in any suitable manner. Thus, for example, finely-divided antimony oxide in a silica-sol can be added to a ball mill and the contents mixed to form a slurry which is, thereafter, evaporated to dryness. The dried composite is then calcined in air. The particle size distribution of the composite is preferably adjusted to match that of the acrylonitrile catalyst particles. Although it is not intended to limit this invention by any particular theory, it is believed that the particles of the antimony oxide-silica composite comprise antimony oxide and silica bound together in some fashion, both mechanically and chemically in the composite particles.

DESCRIPTION OF THE PREFERRED EMBODIMENTS

The process of the present invention involves the selective manufacture of acrylonitrile by passing a gaseous mixture comprising propylene, molecular oxygen and ammonia upwardly through a fluidized bed comprising particles of a highly-active acrylonitrile catalyst and separate and discrete particles comprising an antimony oxide-silica composite. Any form of antimony oxide can be used to form the composite, including $Sb_2O_3$, $Sb_2O_4$ or $Sb_2O_5$.

The antimony oxide-silica composite of the present invention can be prepared in any suitable manner. Thus, finely-divided antimony oxide and a silica-sol (for example, containing from about 30 to about 40 weight percent silica, with most of the rest being water) can be added to a ball mill and the contents mixed to form a slurry and then evaporated to dryness in an oven or a spray dryer. The dried composite is then calcined in air at a temperature in the range of between about 800° to about 1100° C. and atmospheric pressure over a period of about one to about 24 hours. The particle size distribution of the composite is preferably adjusted to match that of the acrylonitrile catalyst, such that at least about 65 percent, preferably at least about 75 percent of the particles are in the range of about 10 to about 300 microns, preferably about 20 to about 200 microns, either by adjusting the spray-drying conditions or by crushing and sieving the calcined composite. Catalyst particles in the 10 to about 300 micron size range are preferred for optimum fluidization. With particles of this size, superficial gas velocities between about 0.5 and about 100 centimeters per second are generally required to achieve a stable fluidized bed. The superficial linear gas velocity is calculated by dividing the volumetric flow rate of the feed gases at reaction conditions by the cross-sectional area of the reactor. The weight ratio of antimony oxide to silica in the composite can vary over a wide range but, in general, will be in the range of about 1:3 to about 3:1, preferably about 1:1.5 to about 1.5:1.

As used in the present application, the expression "highly-active acrylonitrile catalyst" is any catalyst capable of producing acrylonitrile in the presence of propylene, molecular oxygen and ammonia at the rate of at least 0.1 gram of acrylonitrile per gram of catalyst per hour.

Examples of such highly-active acrylonitrile catalysts are described, for example, in U.S. Pat. Nos. 4,040,983 and 4,045,373, as well as U.S. Pat. No. 4,222,899 to Innes et al, the disclosures of which are incorporated by reference. Such highly-active acrylonitrile catalysts include an oxide of uranium and antimony in combination with: (1) tin; (2) a Group IV B metal; or (3) a Group IV B metal in combination with molybdenum and/or vanadium. Thus, such catalysts may be produced, for example, by heating a mixture containing oxides of uranium, antimony and tin in an atmosphere containing molecular oxygen at a temperature of at least 800° or 850° C. for about 15 minutes to about 24 hours. Likewise, compounds of such elements that will be composed or converted to the desired oxides can be utilized.

Examples of oxides that may be heated to form part of the highly-active acrylonitrile catalyst described above include $UO_2$, $U_3O_8$, $UO_3$, $Sb_2O_3$, $Sb_2O_4$, $Sb_2O_5$, $SnO_2$, $SnO$, $USbO_5$, $USb_3O_{10}$ and the like. Examples of compounds that will be converted to these oxides upon heating include $UO_2(NO_3)_2.6H_2O$, $UO_2C_2O_4.3H_2O$, $UO_2(C_2H_3O_2)_2.2H_2O$, $Sb_2(C_4H_4O_6)_3.6H_2O$, $Sb(C_2H_3O_2)_3$, $Sn(NO_3)_4$, $SnC_2O_4$, $SnC_4H_4O_6$, $Ti_2O_3$, $TiO_2$, $ZrO_2$, $HfO_2$, $UTiO_5$, $USbO_5$, $USb_3O_{10}$ and any hydrated oxide or hydroxide of antimony, uranium, titanium, zirconium, hafnium or tin.

Intimate mixing of the above materials greatly facilitates the formation of the desired catalyst. Intimate mixing can be achieved by coprecipitation of the hydroxides or hydrated oxides from acidic solution by adding a suitable base such as ammonium hydroxide. The precipitate so obtained is washed with water, dried at a temperature of 100° to 200° C. for from two to 24 hours and then calcined. The acidic solution is conveniently prepared using various soluble salts as starting materials. These include $UO_2(NO_3)_2.6H_2O$, $UO_2(C_2H_3O_2)_2.2H_2O$, $UCl_3$, $UCl_4$, $UF_6$, $UBr_4$, $SbCl_3$, $Sb(C_2H_3O_2)_3$, $SbF_3$, $SbCl_5$, $SnCl_4$, $SnCl_2.2H_2O$, $Ti_2(C_2O_4)_3.10H_2O$, $ZrOCl_2.8H_2O$, $ZrO(C_2H_3O_2)_2$ and $ZrOBr_2.XH_2O$.

Alternatively, one can prepare acidic solutions from the metals themselves or their oxides. For example, antimony metal can be reacted with concentrated nitric acid to obtain the hydrous oxide, which can be dissolved in concentrated hydrochloric acid.

A preferred highly-active acrylonitrile catalyst for use in the process of the present invention may be defined by the formula:

$$USb_{3-x}A_xO_{8-10} \qquad (I)$$

wherein A is a Group IV B element, x is the number about 0.25 to about 1.50, and thus the amounts of the reactant components used in the preparation of such catalyst must be predetermined so as to provide the atomic ratios of metals and oxygen falling within the foregoing formula. The production of such catalyst is described in U.S. Pat. No. 4,040,983.

Another preferred catalyst is that having the formula:

$$USb_aSn_bO_{8-12} \qquad (II)$$

wherein a is the number about 2.5 to about 1.5 and b is the number about 0.5 to about 1.5, with the atomic ratio of the sum of antimony and tin to uranium being about 2.5:1 to about 3.5:1. Likewise, the amounts of reactant components used in the preparation of this highly-active acrylonitrile catalyst must be in amounts so as to result in the atomic ratios defined in the foregoing formula. The production of such catalyst is described in U.S. Pat. No. 4,045,373.

Still another preferred catalyst for use in the process of the present invention can be defined by the formula:

$$USb_aX_bY_cO_d \qquad (III)$$

wherein X is an element from Group IV B of the Periodic Table; Y is at least one element selected from the group consisting of molybdenum and vanadium; a is a number falling within the range of about 1.35 to about 2.75; b is a number falling within the range of about 0.25 to about 1.65; c is a number falling within the range of about 0.05 to about 0.2; d is a number falling within the range of about 8 to about 12; and the sum of a+b is a number falling within the range of about 2.5 to about 3.5.

The catalyst of formula (III) is similar to that of formula (I) except that it contains either molybdenum or vanadium in addition to the components of formula (I). The production of catalyst (III) is described in U.S. Pat. No. 4,222,899 to Innes et al.

The weight ratio of the antimony oxide-silica composite to the highly-active catalyst can vary over a wide range but, in general, will be in the range of about 0.5:1 to about 20:1, preferably about 1:1 to about 5:1.

As previously indicated, the process of the present invention involves passing propylene, molecular oxygen and ammonia upwardly through a fluidized bed comprising particles of the highly-active acrylonitrile catalyst and particles of the antimony oxide-silica composite. Suitable reaction temperatures include those in the range of between about 350° to about 500° C., preferably between about 400° to about 480° C. Suitable reaction pressures include those in the range of between about 0 to about 50 pounds per square inch gauge (345 kPa), preferably between about 0 and about 30 pounds per square inch gauge (207 kPa) and the contact time, defined as the bulk volume of the catalyst divided by the volumetric feed rate of the gaseous reactants at reaction conditions, between about two to about 20 seconds, generally about four to about 12 seconds. The molar ratio of molecular oxygen to propylene fed to the reactor is in the range of about 0.5:1 to about 10:1, preferably about 1.5:1 to about 2.5:1. The molar ratio of ammonia to propylene ranges from about 0.5:1 to about 10:1, but preferably ranges from about 0.9:1 to about 1.3:1. The preferred active catalysts are those described in U.S. Pat. No. 4,040,983.

The following examples will provide a further understanding of the invention.

EXAMPLE I

This example illustrates the preparation of a suitable composite used herein.

A 76-gram portion of $Sb_2O_5$ was ball milled for two hours with 240 grams of an ammonia-stabilized silica sol containing about 30 percent by weight $SiO_2$ (commercially available as "LUDOX AS" from DuPont). The resultant slurry was heated in an evaporating dish with constant stirring until a thick paste was obtained. The paste was oven dried at 120° C. under atmospheric pressure for eight hours and then calcined at 930° C. in air under atmospheric pressure for two hours. The calcined material was crushed and sieved to obtain a mixture containing 80 to 200 mesh particles. X-ray diffraction and chemical analysis showed this material to be a 50—50 weight percent composite of $Sb_2O_4$ and $SiO_2$.

EXAMPLE II

This example illustrates the use of the composite of Example I in combination with a highly-active acrylonitrile catalyst for producing acrylonitrile.

A highly-active acrylonitrile catalyst containing 50 weight percent $USb_2TiO_{10}$ and 50 weight percent $SiO_2$ was prepared by adding one liter of concentrated hydrochloric acid to a solution containing 114.05 grams of $SbCl_3$ and 125.53 grams of $UO_2(NO_3).6H_2O$. To this solution there was added a solution containing 100.54 grams of titanium sulfate and 2.5 liters of water. Three liters of concentrated ammonium hydroxide were added to the resulting solution and a yellow precipitate formed. The precipitate was recovered by filtration and then washed with 25 liters of water. The filter cake, amounting to 24.8 weight percent solids, was combined with 549.33 grams of LUDOX AS. A ten weight percent solids solution was made by adding 1,942 grams of water to the mixture of filter cake and LUDOX AS. The resultant mixture was sieved through a 30-mesh screen and spray dried. The bottoms and overhead were then mixed and oven dried overnight and then calcined at 910° C. for 16 hours to obtain a product containing 50 weight percent $USb_2TiO_{10}$ and 50 weight percent $SiO_2$.

A 30.4-gram portion of this catalyst was physically admixed with 65.5 grams of the antimony oxide-silica composite of Example I and charged to a fluidized bed reactor having a diameter of 2.4 centimeters and a length of 55.88 centimeters. Air was charged to the bottom of the reactor through a fritted disc, while propylene and ammonia were charged at a point 12.7 centimeters above the fritted disc. A series of duplicate runs was carried out as reported below in Table I. In each run the contact time was about five seconds. Percent conversions and percent selectivities were determined in accordance with the following definitions:

$$\text{Percent Conversion} = \frac{\text{moles of propylene converted}}{\text{moles of propylene fed}} \times 100$$

$$\text{Percent Selectivity} = \frac{\text{moles of acrylonitrile produced}}{\text{moles of propylene reacted}} \times 100.$$

aluminum phosphate were each used in place of the antimony oxide-silica composite in the admixture with the highly-active acrylonitrile catalyst. In each instance selectivity to acrylonitrile was below 50 mole percent and excess amounts of carbon oxides, polymers and other degradation products were formed.

Obviously, many modifications and variations of the invention, as hereinabove set forth, can be made without departing from the spirit and scope thereof and, therefore, only such limitations should be imposed as are indicated in the appended claims.

We claim:

1. A process for preparing acrylonitrile which comprises passing propylene, oxygen and ammonia at an elevated temperature upwardly through a fluidized bed reactor, wherein said bed comprises an admixture of (A) particles of a highly-active acrylonitrile catalyst, said highly-active catalyst being capable of producing acrylonitrile in the presence of propylene, molecular oxygen and ammonia at the rate of at least 0.1 gram of acrylonitrile per gram of catalyst per hour, and (B) particles of a composite consisting essentially of antimony oxide and silica in a weight ratio of antimony oxide to silica of from about 1:3 to about 3:1, the weight ratio of said antimony oxide-silica composite to said highly-active catalyst being in the range of between about 0.5:1 to about 20:1.

2. The process of claim 1, wherein said composite has a weight ratio of antimony oxide to silica from about 1:1.5 to 1.5:1.

3. The process of claim 1, wherein said antimony oxide is $Sb_2O_4$, $Sb_2O_3$ or $Sb_2O_5$.

4. The process of claim 3, wherein said antimony oxide is $Sb_2O_4$.

5. The process of claim 3, wherein said antimony oxide is $Sb_2O_3$.

6. The process of claim 1, wherein a contact time of between about two to about 20 seconds is employed.

7. The process of claim 6, wherein the contact time is between about four to about 12 seconds.

8. The process of claim 1, wherein the reaction temperature is between about 350° to about 500° C.

9. The process of claim 8, wherein the reaction temperature is between about 400° to about 480° C.

10. The process of claim 1, wherein the reaction pressure is between about 0 to about 345 kPa.

TABLE I

|  | Run No. | | | | | | | |
|---|---|---|---|---|---|---|---|---|
|  | 1 | 2 | 3 | 4 | 5 | 6 | 7 | 8 |
| Pressure, kPa | 0 | 0 | 3.45 | 3.45 | 6.9 | 6.9 | 10.3 | 10.3 |
| Temperature, °C. | 480 | 480 | 480 | 480 | 480 | 480 | 480 | 480 |
| Flow Rates, Cubic Centimeters* Per Minute | | | | | | | | |
| Air | 330 | 330 | 440 | 440 | 550 | 550 | 660 | 660 |
| $NH_3$ | 33 | 33 | 44 | 44 | 55 | 55 | 66 | 66 |
| Propylene | 30 | 30 | 40 | 40 | 50 | 50 | 60 | 60 |
| Mole Percent Propylene Converted | 87.5 | 90.4 | 86.1 | 87.1 | 81.5 | 84.6 | 78.6 | 80.5 |
| Mole Percent Selectivity | | | | | | | | |
| $CO + CO_2$ | 7 | 7.4 | 9.2 | 9.8 | 9.5 | 11.1 | 11.5 | 12.0 |
| HCN | 1.1 | 1.0 | 1.3 | 1.3 | 1.3 | 1.4 | 1.5 | 1.6 |
| Acetonitrile | 1.6 | 1.6 | 1.9 | 1.7 | 1.8 | 1.9 | 2.1 | 2.0 |
| Acrylonitrile | 90.2 | 90.0 | 87.6 | 87.0 | 86.1 | 85.2 | 84.7 | 84.1 |

*Measured at standard temperature and pressure

Additionally, runs similar to those of Examples II were carried out wherein gamma alumina, silica gel and 11. The process of claim 10, wherein the reaction pressure is between about 0 to about 270 kPa.

12. The process of claim 1, wherein the weight ratio of the antimony oxide-silica composite to the catalyst is in the range of between about 1:1 to about 5:1.

13. The process of claim 1, wherein the particle size distribution of the antimony oxide-silica composite is substantially the same as that of the acrylonitrile catalyst.

14. The process of claim 1, wherein at least about 65 percent of the composite particles and the catalyst particles are in the range of between about ten to about 300 microns.

15. The process of claim 14, wherein at least about 75 percent of the composite particles and the catalyst particles are in the range of between about 20 to about 200 microns.

16. The process of claim 1, wherein said highly-active acrylonitrile catalyst is defined by the formula:

$$USb_{3-x}A_xO_{9.10}$$

wherein A is a Group IV B element, x is the number from about 0.25 to about 1.50.

17. The process of claim 1, wherein said highly-active acrylonitrile catalyst is defined by the formula:

$$USb_aSn_bO_{8.12}$$

wherein a is the number from about 2.5 to about 1.5 and b is the number from about 0.5 to about 1.5, with the atomic ratio of the sum of the antimony and tin to uranium being from about 2.5:1 to about 3.5:1.

18. The process of claim 1, wherein said highly-active acrylonitrile catalyst is defined by the formula:

$$USb_aX_bY_cO_d$$

wherein X is an element from Group IV B of the Periodic Table; Y is at least one element selected from the group consisting of molybdenum and vanadium; a is a number falling within the range of about 1.35 to about 2.75; b is a number falling within the range of about 0.25 to about 1.65; c is a number falling within the range of about 0.05 to about 0.2; d is a number falling within the range of about 8 to about 12; and the sum of a+b is a number falling within the range of about 2.5 to about 3.5.

19. The process of claim 1, wherein said composite is prepared by
  (a) mixing a finely-divided antimony oxide and a silica-sol to form a slurry;
  (b) drying said slurry; and
  (c) calcining said dried slurry.

* * * * *